United States Patent
Haubrich et al.

(10) Patent No.: US 8,185,210 B2
(45) Date of Patent: May 22, 2012

(54) COMMUNICATION SYSTEM AND METHOD WITH PREAMBLE ENCODING FOR AN IMPLANTABLE MEDICAL DEVICE

(75) Inventors: Gregory J. Haubrich, Champlin, MN (US); Javaid Masoud, Shoreview, MN (US); George C. Rosar, Minneapolis, MN (US); Glenn O. Spital, Granada Hills, CA (US); Quentin S. Denzene, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 487 days.

(21) Appl. No.: 11/224,595

(22) Filed: Sep. 12, 2005

(65) Prior Publication Data
US 2007/0060978 A1    Mar. 15, 2007

(51) Int. Cl.
*A61N 1/00* (2006.01)
*H04K 1/10* (2006.01)
*G06F 12/00* (2006.01)

(52) U.S. Cl. .............. 607/60; 607/30; 607/32; 375/260; 711/1

(58) Field of Classification Search .................. 607/30, 607/32, 60; 375/260; 711/1
See application file for complete search history.

(56) References Cited

U.S. PATENT DOCUMENTS

| | | | |
|---|---|---|---|
| 4,276,618 A | 6/1981 | Green | |
| 4,786,903 A | 11/1988 | Grindahl et al. | |
| 4,799,059 A * | 1/1989 | Grindahl et al. | 340/870.03 |
| 5,324,315 A * | 6/1994 | Grevious | 607/60 |
| 5,350,407 A | 9/1994 | McClure et al. | |
| 5,350,411 A * | 9/1994 | Ryan et al. | 607/32 |
| 5,549,113 A | 8/1996 | Halleck et al. | |
| 5,600,707 A | 2/1997 | Miller, II | |
| 5,752,977 A | 5/1998 | Grevious et al. | |
| 5,843,139 A * | 12/1998 | Goedeke et al. | 607/32 |
| 5,904,708 A | 5/1999 | Goedeke | |
| 5,995,874 A | 11/1999 | Borza | |
| 6,219,580 B1 | 4/2001 | Faltys et al. | |
| 6,223,083 B1 * | 4/2001 | Rosar | 607/60 |
| 6,335,953 B1 | 1/2002 | Sanderford, Jr. et al. | |
| 6,381,492 B1 * | 4/2002 | Rockwell et al. | 607/5 |
| 6,443,891 B1 * | 9/2002 | Grevious | 600/302 |
| 6,631,296 B1 * | 10/2003 | Parramon et al. | 607/61 |
| 6,644,321 B1 | 11/2003 | Behm | |
| 6,687,543 B1 | 2/2004 | Isaac et al. | |

(Continued)

FOREIGN PATENT DOCUMENTS
EP    0717510    6/1996
(Continued)

OTHER PUBLICATIONS

International Search Report, PCT/US2006/035598, Mar. 7, 2007, 5 pages.

(Continued)

*Primary Examiner* — Niketa Patel
*Assistant Examiner* — Nicole F Lavert
(74) *Attorney, Agent, or Firm* — Stephen W. Bauer; Michael J. Ostrom

(57) ABSTRACT

Medical data is communicated from a transmitter of an external unit to a receiver of an implantable medical device. The transmitter generates a preamble signal having encoded configuration data that informs the receiver of configuration settings to be used in receiving the medical data. The receiver detects the preamble and validates a modulation pattern of the preamble. Configuration data is decoded from the preamble signal and the receiver configuration is adjusted to receive the medical data.

23 Claims, 6 Drawing Sheets

U.S. PATENT DOCUMENTS

| | | |
|---|---|---|
| 6,704,602 B2 * | 3/2004 | Berg et al. ............... 607/60 |
| 6,738,670 B1 | 5/2004 | Almendinger et al. |
| 6,829,493 B1 | 12/2004 | Hunzinger |
| 6,897,788 B2 * | 5/2005 | Khair et al. ............ 340/870.16 |
| 6,993,393 B2 | 1/2006 | Von Arx et al. |
| 2001/0012955 A1 * | 8/2001 | Goedeke et al. ............ 607/27 |
| 2002/0026224 A1 | 2/2002 | Thompson et al. |
| 2002/0103514 A1 | 8/2002 | Abrahamson |
| 2002/0123672 A1 * | 9/2002 | Christophersom et al. ... 600/300 |
| 2002/0143372 A1 * | 10/2002 | Snell et al. ............... 607/30 |
| 2002/0183806 A1 * | 12/2002 | Abrahamson et al. .......... 607/60 |
| 2003/0069614 A1 | 4/2003 | Bowman, IV et al. |
| 2003/0097157 A1 * | 5/2003 | Wohlgemuth et al. ......... 607/27 |
| 2003/0114898 A1 | 6/2003 | Von Arx et al. |
| 2003/0187484 A1 * | 10/2003 | Davis et al. ............... 607/60 |
| 2003/0229383 A1 | 12/2003 | Whitehurst et al. |
| 2004/0127959 A1 * | 7/2004 | Amundson et al. ............ 607/60 |
| 2004/0167587 A1 * | 8/2004 | Thompson ............... 607/60 |
| 2004/0172104 A1 * | 9/2004 | Berg et al. ............... 607/60 |
| 2004/0176811 A1 * | 9/2004 | Von Arx et al. ............ 607/32 |
| 2004/0176822 A1 * | 9/2004 | Thompson et al. ............ 607/60 |
| 2005/0249236 A1 | 11/2005 | Walden |
| 2006/0097157 A1 | 5/2006 | Ouyang et al. |
| 2007/0049983 A1 * | 3/2007 | Freeberg ............... 607/32 |

FOREIGN PATENT DOCUMENTS

| | | |
|---|---|---|
| EP | 1264614 | 12/2002 |
| EP | 1495783 | 1/2005 |
| JP | 10256928 | 9/1998 |
| JP | 20042080704 | 7/2004 |
| WO | WO9725100 A | 7/1997 |
| WO | WO0224064 A1 | 3/2002 |
| WO | WO 02024064 * | 9/2002 |
| WO | 0031998 | 11/2003 |
| WO | 03095024 | 11/2003 |

OTHER PUBLICATIONS

International Search Report, PCT/US2006/035597, Jun. 3, 2007, 6 Pages.

* cited by examiner

COMMUNICATION SYSTEM AND METHOD WITH PREAMBLE ENCODING FOR AN IMPLANTABLE MEDICAL DEVICE

CROSS-REFERENCE TO RELATED APPLICATION(S)

Reference is made to the following applications filed on even date: U.S. patent application Ser. No. 11/224,593 (currently pending) entitled "SYSTEM AND METHOD FOR UNSCHEDULED WIRELESS COMMUNICATION WITH A MEDICAL DEVICE," by Gregory J. Haubrich; Len D. Twetan; David Peichel; Charles H. Dudding; George C. Rosar; and Quentin S. Denzene; U.S. patent application Ser. No. 11/224,591 (now patented as U.S. Pat. No. 7,890,181) entitled "SYSTEM AND METHOD FOR UNSCHEDULED WIRELESS COMMUNICATION WITH A MEDICAL DEVICE," by Quentin S. Denzene and George C. Rosar; and U.S. patent application Ser. No. 11/224,594 (currently pending) entitled "IMPLANTABLE MEDICAL DEVICE COMMUNICATION SYSTEM WITH MACRO AND MICRO SAMPLING INTERVALS," by Glenn Spital.

FIELD OF THE INVENTION

The present invention relates generally to implantable medical devices, and more particularly to wireless communication associated with implantable medical devices.

BACKGROUND OF THE INVENTION

Implantable medical devices (IMDs) are now used to provide countless therapies and to monitor a wide variety of physiological events. With the increased uses of IMDs has also come the need for improved methods of communicating with and between IMDs.

Conventionally, communication with IMDs has been with magnetic field communication systems. Such systems, however, are generally only capable of communicating over very short distances, on the order of a few inches. As a result, a magnetic head of a programmer (or other external device) must be located on or near the IMD for communication to occur. More recently, radio frequency (RF) communication systems have been developed for use with IMDs. RF communication provides a number of benefits over magnetic field communication systems, including much greater communication distances.

Because an IMD is surgically implanted within the body of a patient, battery life is one of the considerations in the design of IMD communication systems. Methods of reducing the amount of time that the receiver of an IMD operates can be beneficial in improving.

DETAILED DESCRIPTION

According to an embodiment of the present invention, medical data is communicated between an external unit and an implantable medical device after the communication of a preamble that includes encoded configuration data. The preamble is transmitted by a transmitter of the external unit. A receiver in the implantable medical device detects and validates a modulation pattern present on the preamble signal, and then decodes the configuration data embedded within the preamble signal. Based on the decoded configuration data, the receiver adjusts to the identified receiver configuration to receive the transmission of medical data.

Figure 1:
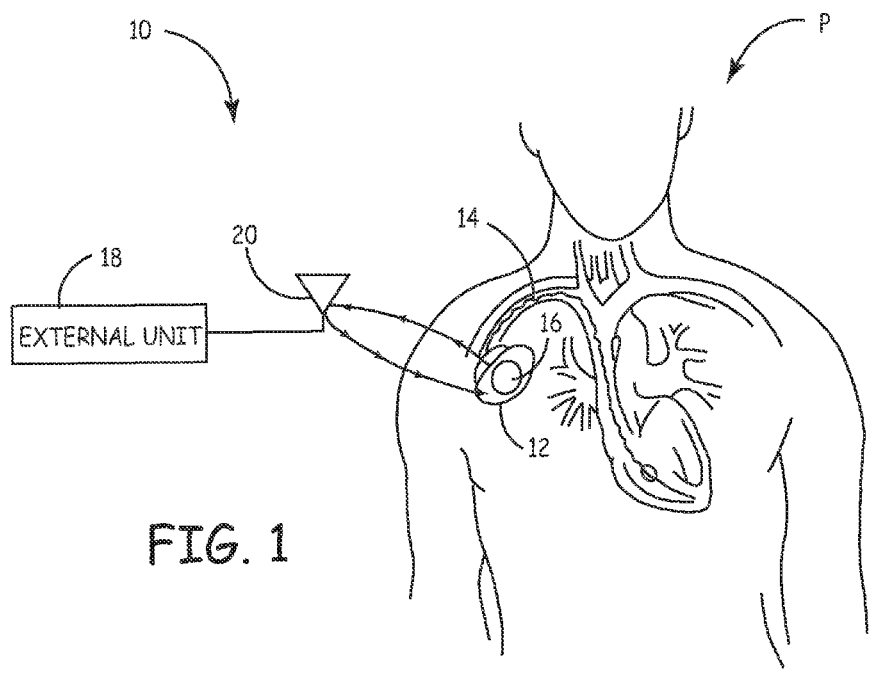
FIG. 1 is a schematic diagram illustrating a communication system for communicating medical data between an implantable medical device (IMD) and an external unit.

FIG. 1 is a schematic diagram illustrating communication system 10 for communication between IMD 12, which includes lead 14 and antenna 16, and external unit 18. In one embodiment, IMD 12 is an implantable cardioverter defibrillator (ICD), but the present invention is equally applicable to many types of medical devices, including both implantable medical devices and external medical devices. IMD 12 is capable of providing therapies and/or sensing physiological events of the heart of patient P via lead 14. Antenna 16 is used to communicate with external unit 18 and may be any device capable of sending or receiving electromagnetic waves, including for example a surface mounted antenna, an inductor, or a half-wave strip.

External unit 18 is a device, such as a programmer, capable of bi-directional communication with IMD 12 via antenna 20. External unit 18 includes antenna 20, which may be any type of RF antenna capable of communicating in the desired RF frequencies with IMD 12, and may be located inside or outside of a housing of external unit 18.

Figure 2:
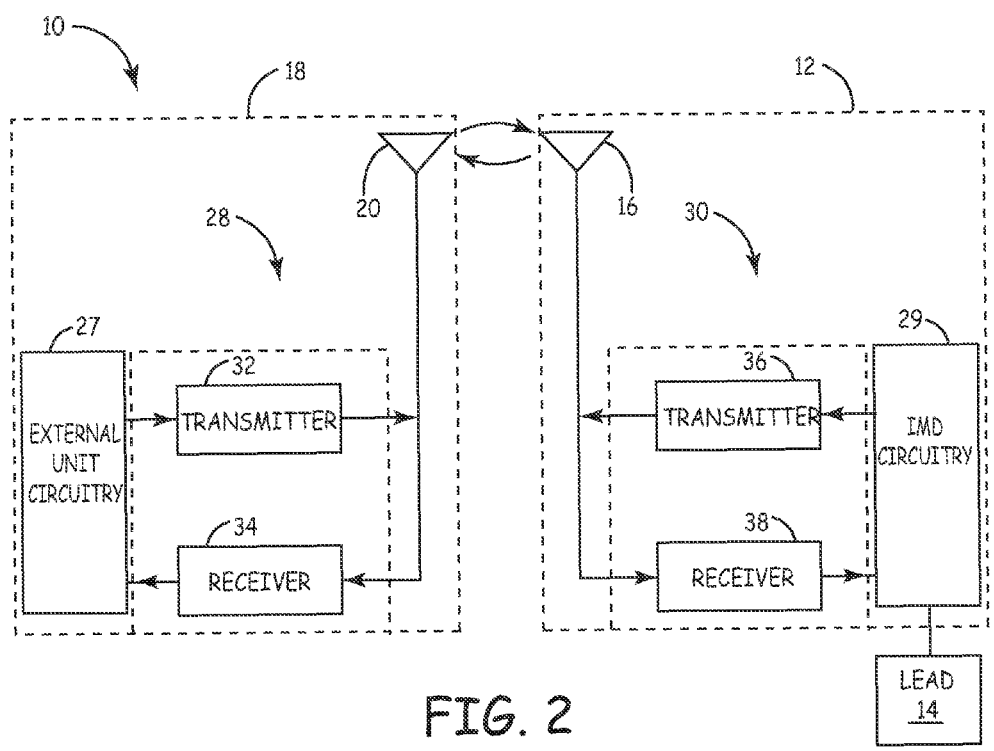
FIG. 2 is a block diagram illustrating the components of the IMD and the external unit that make up the communication system.

FIG. 2 is a block diagram illustrating some of the functional the components of IMD 12 and external unit 18 that make up communication system 10. External unit 18 includes antenna 20, external unit circuitry 27, and transceiver 28. Antenna 20 is coupled to transceiver 28 of external unit 18. External unit circuitry 27 includes a microcomputer and software to control the operation of external unit 18. Transceiver 28, coupled to antenna 20, enables external unit circuitry 27 to transmit and receive communications with IMD 12. Transceiver 28 of external unit 18 includes transmitter 32 and receiver 34.

IMD circuitry 29 includes a microprocessor for controlling the operation of IMD 12 and for processing medical data, therapy delivery circuitry for delivering a therapy through lead 14, and sensors for generating medical data relating to patient P including data generated by detecting electrical signals on lead 14. Transceiver 30, coupled to antenna 16, enables IMD circuitry 29 to transmit and receive communications with external unit 18. Transceiver 30 includes transmitter 36 and receiver 38, which transmit and receive data using RF electromagnetic waves.

Communication between IMD 12 and external unit 18 can be performed over any communication band. In one embodiment, the communication occurs over a public radio frequency band. In another embodiment, the communication occurs over the Medical Implant Communication (MICs) band between 402 MHz and 405 MHz. Although the present invention is described with reference to radio frequency bands, it is recognized that the present invention is also be beneficial with other types of electromagnetic communication.

Because IMD 12 has a finite battery capacity, an important consideration in the design of RF communication system 10 is the energy efficiency of IMD 12. A substantial factor in the energy efficiency of IMD 12 is the time transceiver 30 spends either transmitting or receiving. Thus, any improvement in energy efficiency of transceiver 30 will lead to increased battery life of IMD 12. Energy efficiency is less of an issue in the design of external unit 18, because external unit 18 is generally connected to an external power source such as a 120V AC. Therefore, methods of operating transceivers 28 and 30 that reduce the energy consumption of transceiver 30, even in exchange for additional energy consumption of transceiver 28, are beneficial.

While transmitters only need to be turned on when there is something to transmit, receivers must be turned on much more frequently. No communication can take place unless the receiver is on, at least momentarily, to detect an attempted transmission. To provide a fast response time, a receiver may sample a communication channel as often as twice every second or more. But, a receiver that turns on just twice every second will turn on 172,800 times in one day. A transmitter, on the other hand, may turn on only a handful of times in that same period. Therefore, a reduction in the energy efficiency of a receiver can provide an increase in the effective life of the device.

Returning to communication system 10 of FIG. 2, transmitter 32 assists in reducing the energy consumed by receiver 38 by transmitting a preamble signal prior to the transmission of data. This preamble signal allows receiver 38 to sample the communication channels periodically, rather than having to remain on at all times, while still ensuring that receiver 38 will not miss the transmission of any data. The preamble signal contains a modulation pattern known by receiver 38. If receiver 38 detects energy on a communication band, but finds that it does not contain the known modulation pattern, receiver 38 can shut down knowing that the detected energy is not a communication initiated by transmitter 32 for its benefit. Furthermore, the preamble signal contains embedded data which further improves the energy efficiency of receiver 38. This data informs receiver 38 of configuration settings (such as receiver channel and communication mode) for the subsequent transmission of data. Receiver 38 may continue operating in a low power receiver mode while receiving the embedded data, and then adjust its receiver configuration settings as specified by the embedded data to initiate the higher power receiver mode for receipt of the transmitted data.

Receiver 38 of IMD 12 (described in more detail below with reference to FIGS. 8-9) includes a low-power receiver mode that can simultaneously sample for energy on multiple communication channels. Communication with IMDs often occurs in a communication band including multiple channels, such as the ten channels of the MICs band. By using a wide band receiver mode, receiver 38 can sample all ten channels at once, rather than sampling each channel individually, thereby reducing the number of samples by a factor of ten. Once the preamble signal is received the receiver is directed to the appropriate channel and the appropriate communication mode by data encoded in the preamble signal transmitted by transmitter 32.

Figure 3:
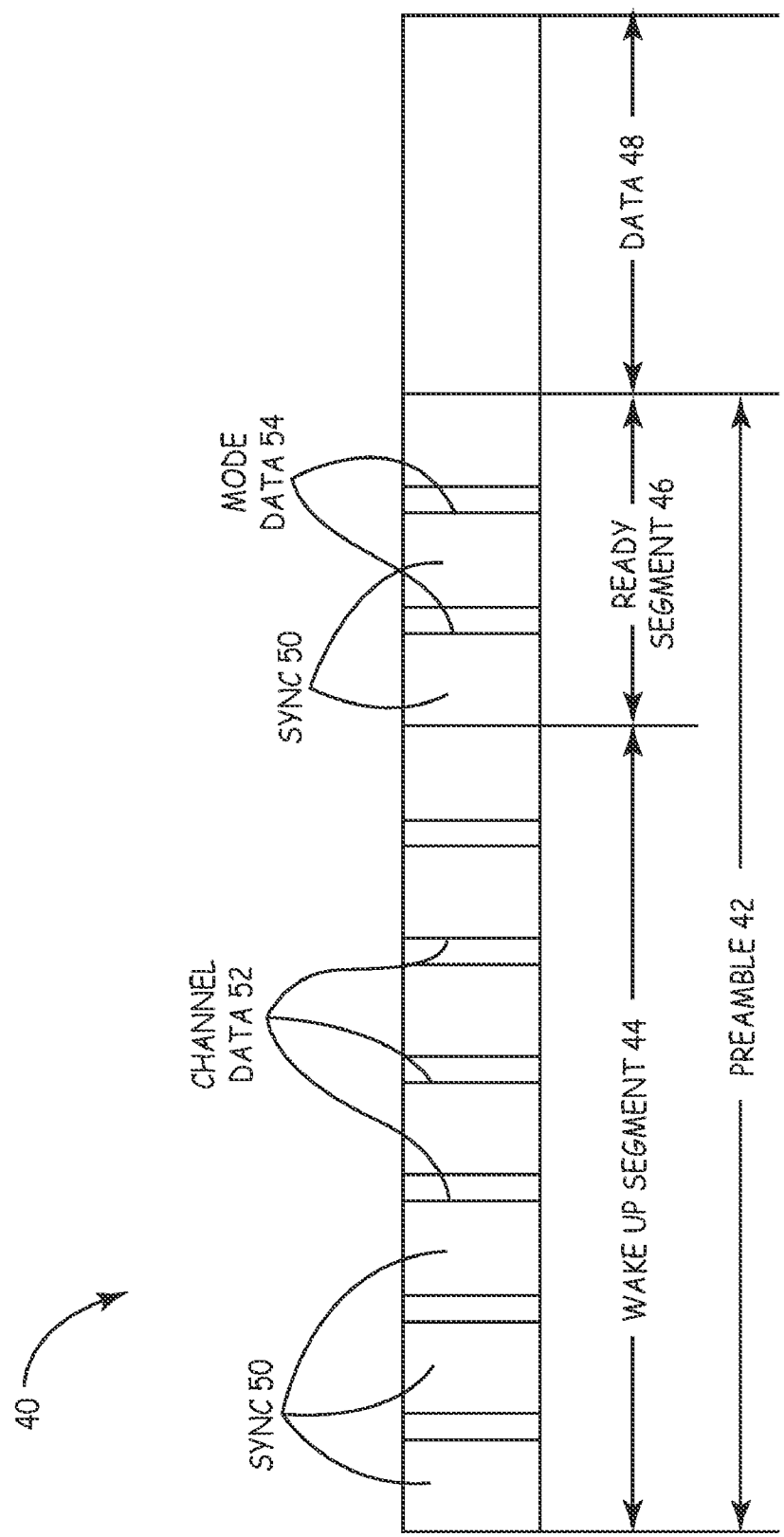
FIG. 3 is a graphical illustration of a transmission bit stream including an encoded preamble and medical data.

FIG. 3 is a graphical illustration of transmission bit stream 40 transmitted by transmitter 32. Transmission bit stream 40 includes preamble signal 42 and data 48. In one embodiment, preamble signal 42 has a duration greater than or equal to a fixed duration, referred to as the macro sampling interval. By transmitting preamble signal 42 for greater duration than the macro sampling interval, receiver 38 can periodically sample received energy for a communication, but turn off between samples. The off-time of receiver 38 conserves energy as compared to having receiver 38 on continuously.

Preamble signal 42 includes wake up segment 44 and ready segment 46. To ensure its detected by receiver 38, wake up segment 44 is the segment that first informs receiver 38 that transmitter 32 desires to communicate with it. Wake up segment 44 is transmitted for a duration greater than the macro sampling interval of receiver 38. Wake up segment 44 includes sync pattern 50 that informs receiver 38 that data 48 is about to be transmitted and embedded channel data 52 that informs receiver 38 on which channel that data is to be transmitted.

Sync pattern 50 is a repeating pattern of bits. In one embodiment, sync pattern 50 is a transmission of alternating on-off keyed (OOK) 0 and 1 bits, each bit having a duration of about 50 microseconds to create a series of repetitive pulses having about 50 microsecond on-time and about 50 microsecond off-time. This transmission results in a transmitted tone having a frequency of about 10 kHz. One of the benefits of OOK sync pattern 50 is that receiver 38 can be designed with a very simple, low-powered OOK or AM receiver capable of detecting the transmission and validating the modulation of the transmission. If energy is detected that does not contain this modulation pattern, receiver 38 can quickly identify the energy as something other than the desired transmission and shut down to conserve energy. Sync pattern may include any recognizable pattern of bits, at any desired bit frequency. Other types of modulation could also be used to validate the modulation pattern, such as amplitude modulation (AM) or vestigial sideband modulation (VSB), phase shift keying (PSK), frequency shift keying (FSK), etc.

During transmission of wake up segment 44, transmitter 32 alternates between transmission of sync pattern 50 and channel data 52. However, channel data 52 is encoded within sync pattern 50 in such a way that the detection and validation components of receiver 38 do not notice the embedded data. In one embodiment, receiver 38 includes a transition detector that detects the leading edges of sync pattern 50, and channel data 52 is embedded in such a way that the leading edges continue in the same pattern as sync pattern 50, but the falling edges are adjusted to encode data. In other words, the pulse width of sync pattern 50 is modified to embed channel data 52 within wake up segment 44. Channel data 52 is described in more detail with reference to FIGS. 4-5 below.

Following wake up segment 44, transmitter 32 transmits ready segment 46 that informs receiver 38 that transmission of data 48 is about to take place and also provides additional encoded configuration data. Ready segment 46 includes sync pattern 50 and mode data 54. In one embodiment, sync pattern 50 of ready segment 46 is phase shifted of 180 degrees from sync pattern 50 of wake up segment 44, such that receiver 38 can differentiate between wake up segment 44 and ready segment 46. In an alternate embodiment, receiver 38 differentiates between wake up segment 44 and ready segment 46 by detecting encoded mode data 54 within ready segment 46. Sync pattern 50 of ready segment 46 can be any other distinct pattern of bits which can be distinguished from sync 50 of wake up segment 44.

Ready segment 46 is transmitted for a period of time greater than a micro sampling interval of receiver 38. After receiver 38 has detected and validated wake up segment 44, and decoded channel data 52, receiver 38 resumes sampling, but now at a shorter interval, referred to as the micro sampling interval. Because ready segment 46 has a greater duration than the micro sampling interval, receiver 38 will detect ready segment 46 prior to the transmission of data 48 from transmitter 32, while still conserving power until detection of ready segment 46.

Embedded within ready segment 46 is encoded mode data 54, which provides receiver operating mode data to receiver 38. This data may include link pertinent information such as desired data rate and/or telemetry protocol for the transmission and reception of data 48. In one embodiment, mode data 54 is embedded within ready segment 46 using frequency shift encoding. Similar to phase shift encoding described above, frequency shift encoding maintains the OOK packet structure of sync pattern 50 to enable receiver 38 to continue detecting and validating the modulation pattern of preamble 42. However, rather than adjusting the pulse width of sync 50, frequency shift encoding adjusts the transmission frequency slightly to encode mode data 54. Frequency shift encoding is further described with reference to FIGS. 6-7.

After transmitter 32 has completed the transmission of preamble 42, data 48 is transmitted. Data 48 may include pure data, messages, requests for a response, and/or any other desired communication between transmitter 32 and receiver 38. All types of data 48 are referred to generally as medical data.

Figure 4:
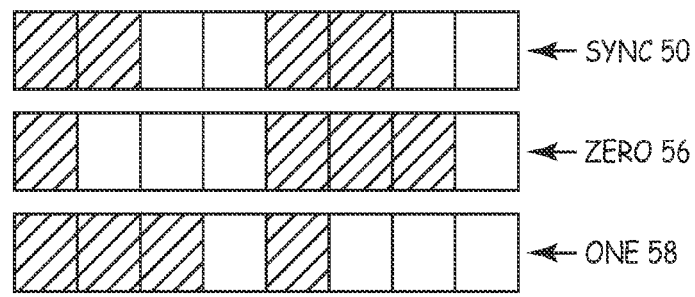
FIG. 4 is a graphical illustration of pulse width encoding.

FIG. 4 is a graphical illustration of one embodiment of a pulse width encoding scheme to encode data within wake up segment 44. Pulse width codes include sync pattern 50, zero pattern 56, and one pattern 58. Sync pattern 50, as previously described, is a repeating pattern of OOK 0 and 1 bits. Each box of FIG. 4 represents one half of a bit length, where a shaded box represents a transmission and an unshaded box represents no transmission. In one embodiment, each bit of sync pattern 50 is 50 microseconds long, such that each box of FIG. 4 represents 25 microseconds.

Pulse width encoding enables data to be encoded within wake up segment 44 without affecting the timing of the leading edges of the bits of the transmission and also maintaining an overall 50% duty cycle. Maintaining a consistent timing of the leading edges allows receiver 38 to verify that the transmitted signal conforms to the appropriate modulation. By adjusting only the trailing edge of the bits, the leading edges remain unchanged.

Zero pattern 56 includes two pulses. Each of the pulses has a leading edge that is equivalent to the leading edge of sync pattern 50. The first pulse has a duration of one-half of a sync bits, and the second pulse has a duration of one and a half of a sync bit. Although the width of the pulses have been varied, the overall duty cycle of zero pattern 56 remains 50%.

One pattern 58 also includes two pulses, with each pulse having a leading edge that is equivalent to the leading edge of sync pattern 50. The first pulse has a duration of one and a half of a sync bit, and the second pulse has a duration of one-half of a sync bit. One pattern 58 also has an overall duty cycle of 50%.

Figure 5:
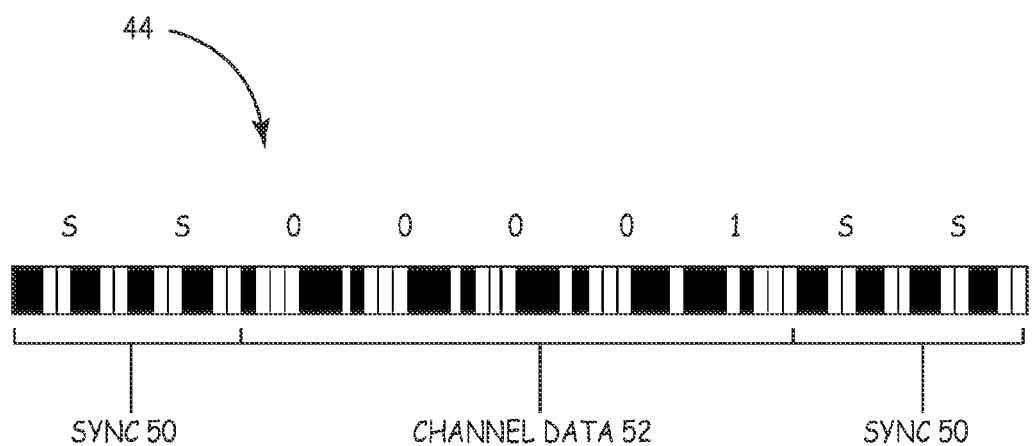
FIG. 5 is a graphical illustration of channel data embedded in the preamble with pulse width encoding.

FIG. 5 is a graphical illustration of channel data encoded with pulse width encoding on a portion of wake up segment 44. The portion of wake up segment 44 shown includes sync pattern 50 (repeated once), five bits of encoded channel data 52, followed by another sync pattern 50 (repeated once). Periodically between transmissions of sync pattern 50, channel data 52 is transmitted.

Channel data 52 allows receiver 38 to sample all channels of a communication band at once with a low power wide band receiver. Once energy has been detected, receiver 38 decodes the communication channel from channel data 52 and adjusts receiver 38 to the appropriate channel. In this way, receiver 38 is able to conserve energy by determining the appropriate communication channel without having to scan each channel individually.

In an embodiment illustrated in FIG. 5, channel data 52 is a binary number of five bits. FIG. 5 shows pulse width encoded channel data of the binary code for channel 1 (00001) transmitted between sync patterns 50. Additional link pertinent information (e.g. data rate, channel, device ID, etc.) could also be transmitted to receiver 38 using the same pulse width encoding technique, if desired. Channel data 52 is repeated periodically within wake up segment 44.

After receiver 38 has received channel data 52 and has adjusted to the appropriate communication channel, it next monitors for ready segment 46 containing mode data 54. Ready segment 46, consists of sync pattern 50 and encoded mode data 54. As described above, in one embodiment, sync pattern 50 of ready segment 46 is shifted 180 degrees from sync pattern 50 of wake up segment 44.

Figures 6, 7:
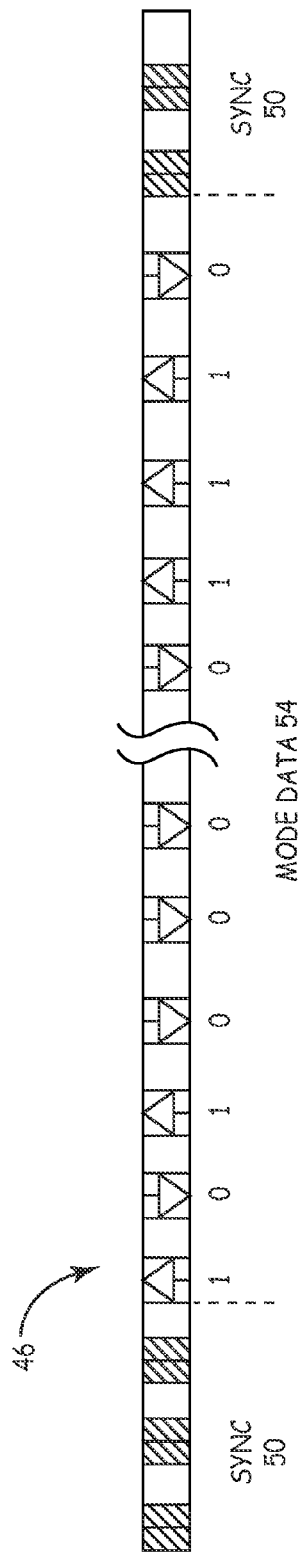
FIG. 6 is a table illustrating frequency shift encoding.
FIG. 7 is a graphical illustration of communication mode data embedded in the preamble with frequency shift encoding.

FIG. 6 is a table illustrating frequency shift encoding of ready segment 46. With receiver 38 adjusted to receive the appropriate communication channel, mode data 54 is communicated to receiver 38 through frequency shift encoding of sync pattern 50. Sync pattern 50, is transmitted at center frequency (fo) of the communication channel. By adjusting this frequency up or down, data can be encoded on ready segment 46, while still maintaining the (phase shifted) leading edges and modulation of sync pattern 50. In one embodiment, data is encoded by shifting sync pattern 50 up or down 100 kHz from center frequency (fo). To transmit a binary zero bit, sync pattern 50 is shifted down 100 kHz from center frequency (fo). This frequency is referred to as low frequency (fL), and is represented graphically by a downward pointing arrow. To transmit a binary one bit, sync pattern 50 is shifted up 100 kHz from center frequency (fo). This frequency is referred to as high frequency (fH), and is represented graphically by an upward pointing arrow.

FIG. 7 is a graphical illustration of a portion of ready segment 46 including frequency shift encoded mode data 54. This portion of ready segment 46 begins with phase shifted sync pattern 50. After sync pattern 50, mode data 54 is encoded within ready segment 46 by shifting the pattern of sync pattern 50 up or down in frequency. Any binary data of any length can be encoded within ready segment 46 using this frequency shift encoding technique. Mode data 54 can be transmitted once or repeated periodically within ready segment 46. In one embodiment, mode data 54 instructs receiver 38 of the appropriate telemetry protocol to use in receiving of medical data 48 from transmitter 32.

Now that transmitter 32 and transmission bit stream 40 have been described, the design and operation of receiver 38 of IMD 12 will be described.

Figure 8:
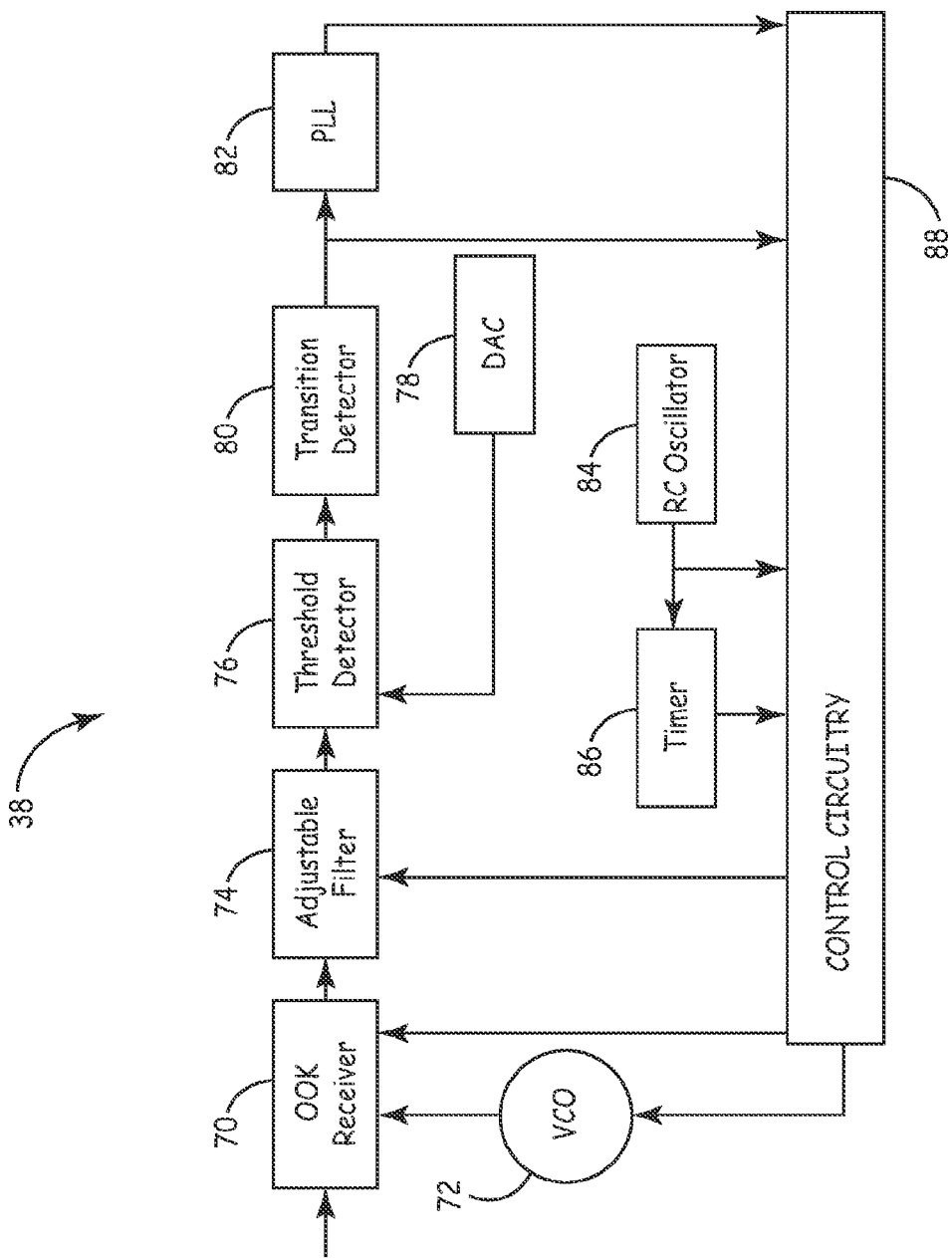
FIG. 8 is a block diagram of a receiver of the IMD.

FIG. 8 is a block diagram of one embodiment of receiver 38 of IMD 12 capable of receiving and processing preamble signal 42. Receiver 38 includes OOK (or AM) receiver 70, voltage controlled oscillator (VCO) 72, adjustable filter 74, threshold detector 76, digital to analog converter (DAC) 78, transition detector 80, phase locked loop (PLL) 82, RC oscillator 84, timer 86, and control circuitry 88.

OOK receiver 70 is a wide band receiver capable of receiving more than one channel at a time. In one embodiment, OOK receiver 70 is an adjustable receiver capable of being adjusted between a wide band mode capable of simultaneously receiving signals on all channels of a communication band and a narrow band mode capable of receiving signals on only a single channel of the communication band. In another embodiment, OOK receiver 70 is a wide band receiver that is operated in parallel with a narrow band receiver such that either or both receivers can be operated at any one time. Receiver 70 can also be another type of receiver, such as an amplitude modulation (AM) receiver. VCO 72 supplies a reference frequency to OOK receiver 70 to tune it to the appropriate receiver frequency.

Following OOK receiver 70 is adjustable filter 74, which is an adjustable low-pass filter used to filter out signals having undesired frequencies. Threshold detector 76, following adjustable filter 74, determines whether the amplitude of the received signal exceeds a threshold amplitude. A reference threshold amplitude is fed into threshold detector by DAC 78. Transition detector 80 follows threshold detector 76 and detects the leading edges of a received signal. Connected to transition detector 80 is PLL tone decoder or correlator 82, which determines how well an input signal correlates with an expected signal and generates a signal adjust VCO 72 as needed.

RC oscillator 84 provides the time base for receiver 38. RC Oscillator 84 and timer 86 work in conjunction to provide appropriate timing signals to logic and state machines within control circuitry 88. Control circuitry 88, which controls the operation of receiver 38, may also include a microprocessor. Control circuitry 88 controls VCO 72, OOK receiver 70, adjustable filter 74, and DAC 78, and receives inputs from various components to enable it to monitor and control the operation of receiver 38. Control circuitry 88 also interfaces with IMD circuitry 29 of IMD 12.

Figure 9:
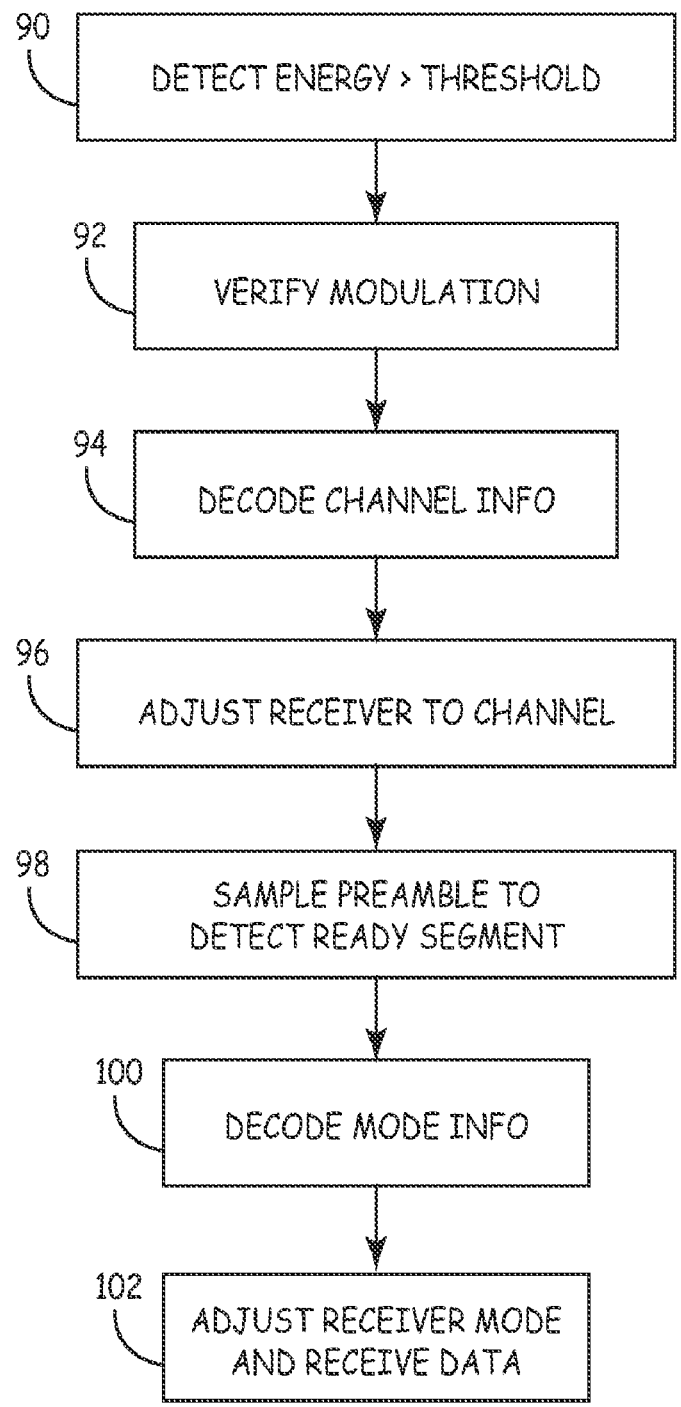
FIG. 9 is a flow chart illustrating a method of operating the receiver.

FIG. 9 is a flow chart illustrating a method of operating receiver 38, begins by sampling the communication band at each macro sampling interval to detect whether the energy present within the communication band exceeds a threshold amplitude (step 90). In this step, receiver 38 operates in a wide band receiver mode to monitor all channels of the communication band at once. Receiver 38 turns on for only as long as needed to determine whether any energy present on the communication band exceeds the threshold amplitude. If no energy is present, receiver 38 turns back off until its next sample at the macro sampling interval.

Once sufficient energy is detected in the communication band, receiver 38 stays on verify whether the detected energy contains the modulation characteristic of preamble signal 42 of transmission bit stream 40 (step 92). To do so, receiver 38 monitors the low-to-high transitions to determine whether the transitions occur at the appropriate rate. For example, if wake up segment 42 is known to contain a 10 kHz bit pattern, receiver 38 monitors the energy to verify whether it corresponds to a 10 kHz pattern. If it does not, then receiver 38 identifies the energy as not being transmission bit stream 40 and turns off until its next sample. If energy is detected that exceeds the threshold amplitude and contains the appropriate modulation, receiver 38 then proceeds on the assumption that the energy present in the communication band is transmission bit stream 40.

After verifying modulation (step 92), receiver 38 remains on to monitor for encoded channel information (step 94) within wake up segment 44. As described above, channel data 52 is encoded within wake up segment 44 with pulse width encoding. Receiver 38 detects the pulse width encoding by monitoring for a series of uncorrelated bits (bits having a different pulse width than sync pattern 50). The uncorrelated bits are identified as channel data 52 and decoded by receiver 38. Decoded channel data 52 informs receiver 38 of the channel in which transmission bit stream 40 is being broadcast by transmitter 32.

Knowing the appropriate channel, receiver 38 adjusts to that communication channel (step 96). At the same time, receiver 38 is adjusted from the wide band receiver mode to a narrow band receiver mode in which only the single channel identified by decoded channel data 52 is received.

Following the adjustment to the appropriate channel, receiver 38 continues to monitor the channel for ready segment 46 (step 98). Since wake up segment 44 is longer than the macro sampling interval of receiver 38, transmission of wake up segment 44 will generally not be complete by the time that receiver 38 has adjusted to the appropriate channel. If no further data is needed from wake up segment 44, receiver 38 has no need to continue receiving the rest of wake up segment 44. Accordingly, receiver 38 turns itself off for short periods of time but periodically turns back on to sample wake up segment 44. The interval of time between samples when looking for ready segment 46 is referred to as the micro sampling interval, which is a period of time less than the duration of ready segment 46.

During each micro sample, receiver 38 determines whether wake up segment 44 is still being transmitted or whether transmission of ready segment 46 has begun (step 98). If wake up segment 44 is still being transmitted, receiver 38 turns off and resumes micro sampling until receiver 38 detects ready segment 46. Detection of ready segment 46 may be, for example, by detecting a phase change or a frequency change.

Once ready segment 46 has been detected, receiver 38 stays on to monitor ready segment 46 for encoded mode data 54. As described above, mode data 54 is encoded with frequency shift encoding. Receiver 38 detects mode data 54 by monitoring for a frequency shift in sync pattern 50, either up or down from center frequency (fo). When mode data 54 is detected it is decoded by receiver 38 (step 100). Mode data 54 instructs receiver 38 of the appropriate receiver mode for reception of data 48. Receiver 38 then adjusts to the appropriate receiver mode identified by mode data 54 (step 102). In one embodiment, the subsequent receiver modes (used to receive data 48) consume more energy. By enabling receiver 38 to detect and evaluate initial communications, and to receive channel and mode data, all prior to entering the high power communication mode, valuable energy savings are realized.

With receiver 38 now set to receive transmission bit stream 40 on the appropriate communication channel, and also configured to the appropriate receiver mode, transmitter 32 transmits data 48. Receiver 38 receives data 48 (step 102) and determines whether any further action is required. If data 48 contains a request for further communication, for example, receiver 38 passes that request to IMD circuitry 29 of IMD 12 which responds accordingly.

Although the present invention has been described with reference to preferred embodiments, workers skilled in the art will recognize that changes may be made in form and detail without departing from the spirit and scope of the invention. In particular, one skilled in the art will recognize that although the present invention has been described for transmissions from an external device to an implantable medical device, it could also be implemented between implantable devices, between external units, among a wireless network of implantable and external devices, or for transmissions from implantable medical devices to external units. In addition, other known types of data encoding could be used to perform the same functions as pulse width encoding and frequency shift encoding described above.

What is claimed is:

1. A medical device for validating and receiving a preamble signal and for receiving a transmission of medical data, the medical data comprising: a device circuitry configured to control the operation of the medical device and for processing the medical data; and a receiver configure to validate a modulation pattern of the preamble signal, extracting configuration data that identifies one of a plurality of communication channels from within the preamble signal, and adjusting the receiver to the communication channel identified in the configuration data.

2. The medical device of claim 1, wherein the extracting configuration data comprises decoding pulse-width encoded data.

3. The medical device of claim 2, wherein the receiver interprets a longer pulse width followed by a shorter pulse width as a binary 1, and interprets a shorter pulse width followed by a longer pulse width as a binary 0.

4. The medical device of claim 1, wherein the receiver extracts the configuration data identifying the one of a plurality of communication channels from a wakeup segment of the preamble signal.

5. The medical device of claim 1, wherein extracting configuration data comprises decoding frequency-shift encoded data.

6. The medical device of claim 5, wherein the receiver interprets a higher frequency pulse as a binary 1, and interprets a lower frequency pulse as a binary 0.

7. The medical device of claim 1, wherein the receiver extracts configuration data that identifies link pertinent information from within the preamble signal and the receiver adjusts in accordance with the link pertinent information to receive the transmission of medical data.

8. The medical device of claim 1, wherein the receiver is configured to periodically turn on to determine whether any energy present on a communication band exceeds a threshold amplitude and turn off in response to determining any energy present does not exceed the threshold amplitude.

9. The medical device of claim 1, wherein the receiver extracts the configuration data that identifies the one of a plurality of communication channels from a wakeup segment of the preamble signal and extracts the configuration data that identifies the link pertinent information from a ready segment of the preamble signal.

10. The medical device of claim 1, wherein the receiver includes detection and validation components for detecting and validating the preamble signal and the configuration data is embedded such that the detection and validation components of the receiver do not notice the embedded configuration data.

11. The medical device of claim 10, wherein leading edges of the configuration data embedded in the preamble signal continue in the same pattern as leading edges of a sync pattern of the preamble signal such that a transition detector of the receiver does not notice the embedded data.

12. The medical device of claim 11, wherein the falling edges of the sync pattern of the preamble signal are adjusted to encode the configuration data.

13. The medical device of claim 7, wherein the link pertinent information comprises one or more of a data rate and a telemetry protocol.

14. A method comprising:
receiving a preamble signal;
validating a modulation pattern of the preamble signal;
extracting configuration data that identifies one of a plurality of communication channels from within the preamble signal;
adjusting the receiver to the communication channel identified in the configuration data;
receiving the subsequent transmission of medical data; and
processing the medical data.

15. The method of claim 14, wherein extracting the configuration data that identifies the one of the plurality of communications channels comprises extracting the configuration data that identifies the one of a plurality of communication channels from a wakeup segment of the preamble signal.

16. The method of claim 14, further comprising:
extracting configuration data that identifies link pertinent information from within the preamble signal; and
adjusting the configuration of the receiver according to the link pertinent information to receive the transmission of medical data.

17. The method of claim 16, wherein
extracting configuration data that identifies the one of a plurality of communication channels comprises extracting configuration data that identifies the one of a plurality of communication channels from a wakeup segment of the preamble signal, and
extracting configuration data that identifies link pertinent information comprises extracting the configuration data that identifies the link pertinent information from a ready segment of the preamble signal.

18. The method of claim 14, wherein validating the modulation pattern of the preamble signal comprises validating the modulation pattern of the preamble signal without noticing the embedded configuration data.

19. The method of claim 14, wherein leading edges of the configuration data embedded in the wakeup signal continue in the same pattern as leading edges of a sync pattern of the wakeup signal and extracting the configuration data comprises decoding the configuration data based on falling edges of the sync pattern of the preamble signal.

20. A medical device comprising:
means for receiving a preamble signal;
means for validating a modulation pattern of the preamble signal;
means for extracting configuration data that identifies one of a plurality of communication channels from within the preamble signal;
means for adjusting the receiver to the communication channel identified in the configuration data;

21. The medical device of claim 20, wherein
the extracting means extract additional configuration data that identifies link pertinent information from within the preamble signal; and
the adjusting means adjust the configuration of the receiving means according to the additional configuration data to receive the transmission of the medical data.

22. The medical device of claim 21, wherein the extracting means extracts the configuration data that identifies the communication channel from a wakeup segment of the preamble signal and extracts the configuration data that identifies link pertinent information from a ready segment of the preamble signal.

23. The medical device of claim 20, wherein the validating means validate the modulation pattern of the preamble signal without noticing the embedded data.

* * * * *